United States Patent
Honegger et al.

(10) Patent No.: US 11,844,563 B2
(45) Date of Patent: Dec. 19, 2023

(54) ENERGY-BASED SURGICAL INSTRUMENTS INCORPORATING COOLING FEATURES

(71) Applicant: Covidien LP, Mansfield, MA (US)

(72) Inventors: Allen Honegger, Berthoud, CO (US); David Van Tol, Boulder, CO (US); Michael B. Lyons, Boulder, CO (US)

(73) Assignee: Covidien LP, Mansfield, MA (US)

( * ) Notice: Subject to any disclaimer, the term of this patent is extended or adjusted under 35 U.S.C. 154(b) by 445 days.

(21) Appl. No.: 17/028,335

(22) Filed: Sep. 22, 2020

(65) Prior Publication Data

US 2021/0145508 A1 May 20, 2021

Related U.S. Application Data (60) Provisional application No. 62/937,659, filed on Nov. 19, 2019.

(51) Int. Cl.
*A61B 17/32* (2006.01)
*A61B 18/14* (2006.01)
*A61B 18/00* (2006.01)

(52) U.S. Cl.
CPC .. *A61B 18/1445* (2013.01); *A61B 17/320068* (2013.01); *A61B 2017/320094* (2017.08); *A61B 2018/00011* (2013.01); *A61B 2018/0019* (2013.01); *A61B 2018/00029* (2013.01); *A61B 2018/0063* (2013.01); *A61B 2018/00595* (2013.01); *A61B 2018/00601* (2013.01)

(58) Field of Classification Search
CPC ........ A61B 18/1445; A61B 17/320068; A61B 2017/320094; A61B 2018/00011; A61B 2018/00029; A61B 2018/0019; A61B 2018/00595; A61B 2018/00601; A61B 2018/0063
See application file for complete search history.

(56) References Cited

U.S. PATENT DOCUMENTS

| | | |
|---|---|---|
| 3,589,363 A | 6/1971 | Banko et al. |
| 4,016,882 A | 4/1977 | Broadwin et al. |
| 4,223,676 A | 9/1980 | Wuchinich et al. |
| 4,587,958 A | 5/1986 | Noguchi et al. |
| 4,660,573 A | 4/1987 | Brumbach |

(Continued)

FOREIGN PATENT DOCUMENTS

WO 2009088390 A1 7/2009

OTHER PUBLICATIONS

Extended European Search Report issued in corresponding European Application No. 20207706.1 dated Mar. 31, 2021, 9 pages.

*Primary Examiner* — Jaymi E Della
(74) *Attorney, Agent, or Firm* — Carter, DeLuca & Farrell LLP (57) ABSTRACT

An ultrasonic surgical instrument includes an ultrasonic waveguide defining a blade at a distal end portion thereof. The ultrasonic waveguide is configured to transmit ultrasonic energy therealong to the blade. The blade defines a plurality of surfaces. At least one lumen is defined at least partially through the blade. The at least one lumen establishes a flow path through the blade extending from a first open end on one surface of the plurality of surfaces to a second open end on a different surface of the plurality of surfaces. The at least one lumen is configured to urge fluid through the blade along the flow path from the one surface to the different surface.

13 Claims, 4 Drawing Sheets

(56) References Cited

U.S. PATENT DOCUMENTS

| | | |
|---|---|---|
| 4,681,561 A | 7/1987 | Hood et al. |
| 4,724,834 A | 2/1988 | Alperovich et al. |
| 4,754,760 A | 7/1988 | Fukukita et al. |
| 4,832,022 A | 5/1989 | Tjulkov et al. |
| 4,832,683 A | 5/1989 | Idemoto et al. |
| 5,076,276 A | 12/1991 | Sakurai et al. |
| 5,163,433 A | 11/1992 | Kagawa et al. |
| 5,188,102 A * | 2/1993 | Idemoto ............. A61M 3/0279 606/45 |
| 5,205,817 A | 4/1993 | Idemoto et al. |
| 5,211,625 A | 5/1993 | Sakurai et al. |
| 5,221,282 A | 6/1993 | Wuchinich |
| 5,261,922 A | 11/1993 | Hood |
| 5,358,505 A | 10/1994 | Wuchinich |
| 5,383,876 A | 1/1995 | Nardella |
| 5,391,144 A | 2/1995 | Sakurai et al. |
| 5,419,761 A | 5/1995 | Narayanan et al. |
| 5,462,522 A | 10/1995 | Sakurai et al. |
| 5,486,162 A | 1/1996 | Brumbach |
| 5,560,362 A | 10/1996 | Sliwa, Jr. et al. |
| 5,624,393 A | 4/1997 | Diamond |
| 5,797,931 A | 8/1998 | Bito et al. |
| 5,879,363 A | 3/1999 | Urich |
| 5,906,628 A | 5/1999 | Miyawaki et al. |
| 6,073,492 A | 6/2000 | Rosselson et al. |
| 6,120,519 A | 9/2000 | Weber et al. |
| 6,206,876 B1 | 3/2001 | Levine et al. |
| 6,315,215 B1 | 11/2001 | Gipson et al. |
| 6,379,371 B1 | 4/2002 | Novak et al. |
| 6,380,264 B1 | 4/2002 | Jameson et al. |
| 6,383,183 B1 | 5/2002 | Sekino et al. |
| 6,443,969 B1 | 9/2002 | Novak et al. |
| 6,454,781 B1 | 9/2002 | Witt et al. |
| 6,551,337 B1 | 4/2003 | Rabiner et al. |
| 6,611,699 B2 * | 8/2003 | Messing ............. A61B 18/1492 606/49 |
| 6,633,234 B2 | 10/2003 | Wiener et al. |
| 6,764,487 B2 | 7/2004 | Mulier et al. |
| 6,770,071 B2 | 8/2004 | Woloszko et al. |
| 6,810,585 B2 | 11/2004 | Hickok |
| 6,923,421 B2 | 8/2005 | Raftis |
| 6,939,350 B2 | 9/2005 | Phan |
| 7,074,219 B2 | 7/2006 | Levine et al. |
| 7,273,483 B2 | 9/2007 | Wiener et al. |
| 7,404,816 B2 | 7/2008 | Abboud et al. |
| 7,530,986 B2 | 5/2009 | Beaupre et al. |
| 7,572,268 B2 | 8/2009 | Babaev |
| 8,348,880 B2 | 1/2013 | Messerly et al. |
| 8,546,996 B2 | 10/2013 | Messerly et al. |
| 8,628,534 B2 | 1/2014 | Jones et al. |
| 8,641,609 B2 | 2/2014 | Hestad et al. |
| 8,641,658 B1 | 2/2014 | Banko |
| 8,679,114 B2 | 3/2014 | Chapman et al. |
| 8,974,478 B2 | 3/2015 | Ross et al. |
| 9,044,261 B2 | 6/2015 | Houser |
| 9,050,124 B2 | 6/2015 | Houser |
| 9,113,930 B2 | 8/2015 | Reid, Jr. |
| 9,113,943 B2 | 8/2015 | Ross et al. |
| 9,211,137 B2 | 12/2015 | Voic |
| 9,271,751 B2 | 3/2016 | Houser et al. |
| 9,276,300 B2 | 3/2016 | Mueller |
| 9,320,528 B2 | 4/2016 | Voic et al. |
| 9,387,005 B2 | 7/2016 | Voic |
| 9,622,767 B2 | 4/2017 | Stoddard et al. |
| 9,737,735 B2 * | 8/2017 | Dietz ................ A61M 37/0092 |
| 10,456,156 B2 | 10/2019 | Stoddard et al. |
| 2002/0087157 A1 | 7/2002 | Sliwa et al. |
| 2002/0091404 A1 | 7/2002 | Beaupre |
| 2003/0181904 A1 | 9/2003 | Levine et al. |
| 2003/0204199 A1 | 10/2003 | Novak et al. |
| 2004/0087972 A1 | 5/2004 | Mulholland et al. |
| 2005/0209578 A1 | 9/2005 | Christian Evans et al. |
| 2006/0195106 A1 | 8/2006 | Jones et al. |
| 2006/0265035 A1 | 11/2006 | Yachi et al. |
| 2007/0233054 A1 | 10/2007 | Babaev |
| 2008/0015563 A1 | 1/2008 | Hoey et al. |
| 2008/0058845 A1 | 3/2008 | Shimizu et al. |
| 2008/0281200 A1 | 11/2008 | Voic et al. |
| 2009/0036914 A1 * | 2/2009 | Houser .................. A61B 17/29 606/169 |
| 2009/0306550 A1 | 12/2009 | Babaev |
| 2010/0274236 A1 | 10/2010 | Krimsky |
| 2010/0298743 A1 | 11/2010 | Nield et al. |
| 2012/0253371 A1 | 10/2012 | Ross et al. |
| 2013/0072950 A1 | 3/2013 | Ross et al. |
| 2013/0090576 A1 * | 4/2013 | Stulen ............ A61B 17/320092 601/2 |
| 2013/0178842 A1 | 7/2013 | Reid, Jr. |
| 2013/0184729 A1 | 7/2013 | Yasunaga |
| 2014/0135804 A1 | 5/2014 | Weisenburgh et al. |
| 2014/0276369 A1 | 9/2014 | Banko |
| 2014/0276740 A1 | 9/2014 | Larson et al. |
| 2015/0073457 A1 * | 3/2015 | Stoddard ........ A61B 17/320092 606/169 |
| 2015/0073458 A1 | 3/2015 | Stoddard et al. |
| 2015/0088137 A1 | 3/2015 | Manna |
| 2015/0148834 A1 | 5/2015 | Gee et al. |
| 2015/0157356 A1 | 6/2015 | Gee |
| 2015/0165240 A1 | 6/2015 | Stoddard et al. |
| 2015/0297255 A1 | 10/2015 | Fan et al. |
| 2016/0082292 A1 | 3/2016 | Kudo |
| 2016/0089155 A1 | 3/2016 | Lark et al. |
| 2016/0129285 A1 | 5/2016 | Mikus et al. |
| 2016/0143657 A1 | 5/2016 | Stera et al. |
| 2016/0143658 A1 | 5/2016 | Stokes et al. |
| 2016/0143659 A1 | 5/2016 | Glutz et al. |
| 2016/0144204 A1 | 5/2016 | Akagane |
| 2016/0195450 A1 | 7/2016 | Akagane |
| 2017/0340345 A1 * | 11/2017 | Yates ............. A61B 17/320068 |
| 2018/0055530 A1 * | 3/2018 | Messerly ......... A61B 17/00234 |

\* cited by examiner

ENERGY-BASED SURGICAL INSTRUMENTS INCORPORATING COOLING FEATURES

CROSS-REFERENCE TO RELATED APPLICATIONS

This application claims the benefit of and priority to U.S. Provisional Patent Application Ser. No. 62/937,659 filed Nov. 19, 2019, the entire disclosure of which is incorporated by reference herein.

FIELD

The present disclosure relates to surgical instruments and, more particularly, to energy-based surgical instruments such as ultrasonic surgical instruments incorporating cooling features to, for example, facilitate ultrasonic blade cooling.

BACKGROUND

Ultrasonic surgical instruments utilize ultrasonic energy, i.e., ultrasonic vibrations, to treat tissue. More specifically, ultrasonic surgical instruments utilize mechanical vibration energy transmitted at ultrasonic frequencies to coagulate, cauterize, fuse, seal, cut, desiccate, fulgurate, or otherwise treat tissue.

Typically, an ultrasonic surgical instrument is configured to transmit ultrasonic energy produced by a generator and transducer assembly along a waveguide to a blade that is spaced-apart from the generator and transducer assembly. With respect to cordless ultrasonic instruments, for example, a portable power source, e.g., a battery, and the generator and transducer assembly are mounted on the handheld instrument itself, while the waveguide interconnects the generator and transducer assembly and the end effector. Wired ultrasonic instruments operate in similar fashion except that, rather than having the generator and power source mounted on the handheld instrument itself, the handheld instrument is configured to connect to a standalone power supply and/or generator via a wired connection.

SUMMARY

As used herein, the term "distal" refers to the portion that is described which is further from a user, while the term "proximal" refers to the portion that is being described which is closer to a user. Further, any or all of the aspects described herein, to the extent consistent, may be used in conjunction with any or all of the other aspects described herein.

Provided in accordance with aspects of the present disclosure is an ultrasonic surgical instrument including an ultrasonic waveguide defining a blade at a distal end portion thereof. The ultrasonic waveguide is configured to transmit ultrasonic energy therealong to the blade. The blade defines a plurality of surfaces. At least one lumen is defined at least partially through the blade. The at least one lumen establishes a flow path through the blade extending from a first open end on one surface of the plurality of surfaces to a second open end on a different surface of the plurality of surfaces. The at least one lumen is configured to urge fluid through the blade along the flow path from the one surface to the different surface, e.g., facilitating cooling of the blade.

In an aspect of the present disclosure, the at least one lumen includes a first lumen extending from the first open end to the second open end.

In another aspect of the present disclosure, the at least one lumen includes a plurality of lumens. Each lumen of the plurality of lumens extends from the first open end to the second open end such that the plurality of lumens define a plurality of flow paths between the first open end and the second open end.

In another aspect of the present disclosure, wherein the at least one lumen includes at least two lumens. A first lumen of the at least two lumens extends from the first open end and a second lumen of the at least two lumens extends from the second open end. The at least two lumens are disposed in communication with one another to define the flow path extending between the first open end and the second open end. In such aspects, the first and second lumens may be directly connected or may be interconnected by a third lumen of the at least two lumens. The first and second lumens may be branch lumens while the third lumen is a trunk lumen.

In yet another aspect of the present disclosure, the one surface is a top surface of the blade and the different surface is a bottom surface of the blade.

In still another aspect of the present disclosure, the one surface is a first side surface of the blade and the different surface is a second, opposite side surface of the blade.

In still yet another aspect of the present disclosure, the ultrasonic surgical instrument further includes a jaw member pivotable relative to the blade between an open position and a clamping position for clamping tissue between the jaw member and the one surface of the blade. In such aspects, the different surface may be opposite the one surface.

In another aspect of the present disclosure, the ultrasonic surgical instrument further includes a transducer coupled to the ultrasonic waveguide at a proximal end portion of the ultrasonic waveguide. The transducer is configured to produce the ultrasonic energy for transmission along the ultrasonic waveguide to the blade.

Another ultrasonic surgical instrument provided in accordance with the present disclosure includes an ultrasonic waveguide defining a blade at a distal end portion thereof. The ultrasonic waveguide is configured to transmit ultrasonic energy therealong to the blade. The blade defines a plurality of surfaces. A plurality of spaced-apart lumens is defined through the blade. Each lumen of the plurality of spaced-apart lumens establishes a flow path through the blade extending from a first open end on one surface of the plurality of surfaces to a second open end on a different surface of the plurality of surfaces. Each lumen of the plurality of spaced-apart lumens is configured to urge fluid through the blade along the corresponding flow path from the one surface to the different surface, e.g., facilitating cooling of the blade.

In an aspect of the present disclosure, the one surface is a top surface of the blade and the different surface is a bottom surface of the blade.

In another aspect of the present disclosure, the ultrasonic surgical instrument further includes a jaw member pivotable relative to the blade between an open position and a clamping position for clamping tissue between the jaw member and the one surface of the blade. In such aspects, the different surface may be opposite the one surface.

In yet another aspect of the present disclosure, the ultrasonic surgical instrument further includes a transducer coupled to the ultrasonic waveguide at a proximal end portion of the ultrasonic waveguide. The transducer is configured to produce the ultrasonic energy for transmission along the ultrasonic waveguide to the blade.

Another ultrasonic surgical instrument provided in accordance with the present disclosure includes an ultrasonic waveguide defining a blade at a distal end portion thereof. The ultrasonic waveguide is configured to transmit ultrasonic energy therealong to the blade. The blade defines a plurality of surfaces. At least one trunk lumen is defined at least partially through the blade. At least one branch lumen is defined at least partially through the blade. The at least one trunk lumen and the at least one branch lumen cooperate to define at least one flow path through the blade extending from a first open end on one surface of the plurality of surfaces to a second open end on a different surface of the plurality of surfaces. The at least one trunk lumen and the at least one branch lumen are configured to cooperate to urge fluid through the blade along the at least one flow path from the one surface to the different surface, e.g., facilitating cooling of the blade.

In an aspect of the present disclosure, the ultrasonic surgical instrument further includes a jaw member pivotable relative to the blade between an open position and a clamping position for clamping tissue between the jaw member and the one surface of the blade. In such aspects, the different surface may be opposite the one surface.

In yet another aspect of the present disclosure, the ultrasonic surgical instrument further includes a transducer coupled to the ultrasonic waveguide at a proximal end portion of the ultrasonic waveguide. The transducer is configured to produce the ultrasonic energy for transmission along the ultrasonic waveguide to the blade.

BRIEF DESCRIPTION OF THE DRAWINGS

The above and other aspects and features of the present disclosure will become more apparent in light of the following detailed description when taken in conjunction with the accompanying drawings wherein like reference numerals identify similar or identical elements.

DETAILED DESCRIPTION

Figure 1:
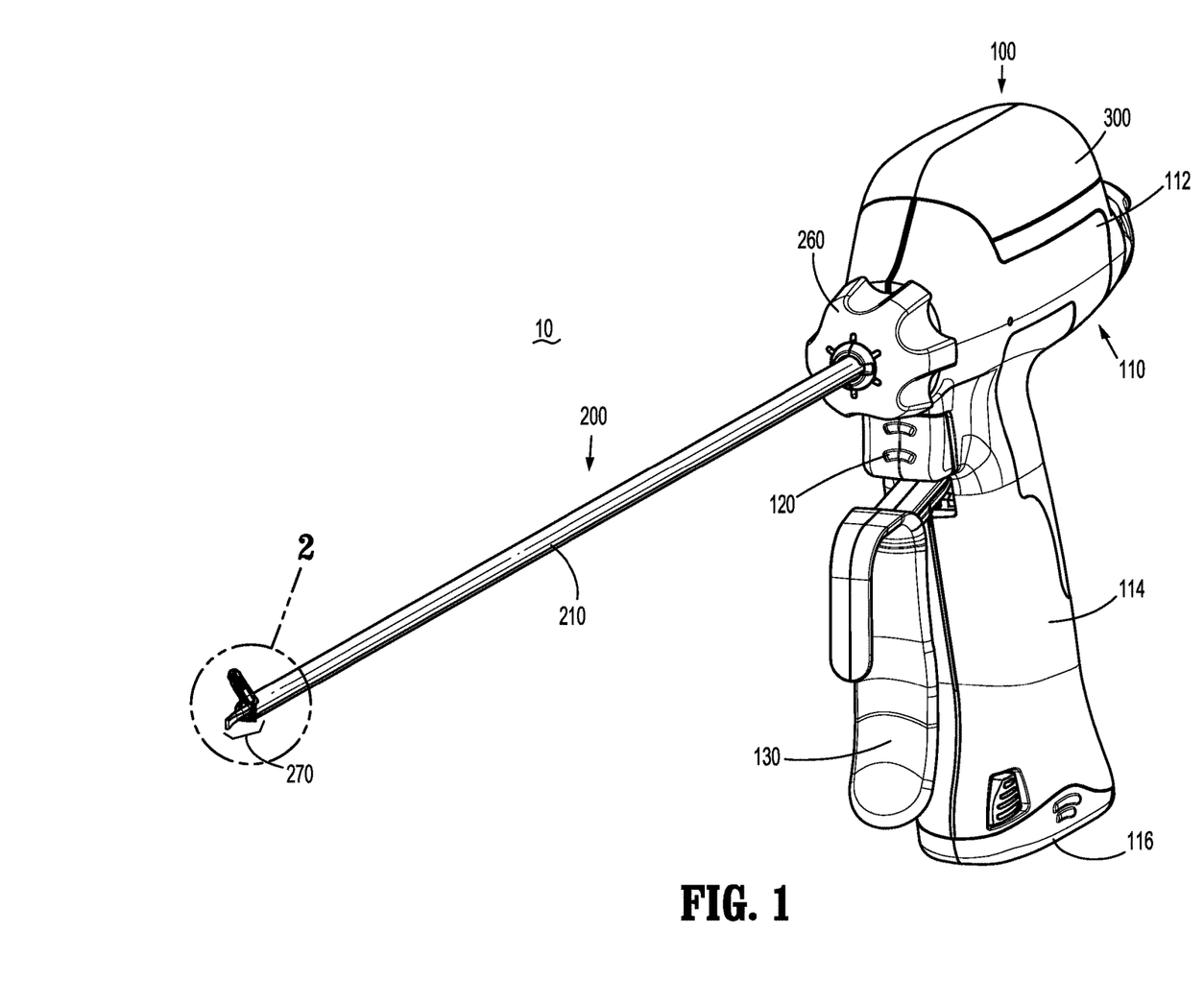
FIG. 1 is a front, perspective view of an ultrasonic surgical instrument provided in accordance with the present disclosure.

Referring generally to FIG. 1, an ultrasonic surgical instrument provided in accordance with the aspects and features of the present disclosure is shown generally identified by reference numeral 10. Although detailed with respect to ultrasonic surgical instrument 10, the aspects and features of the present disclosure are equally applicable for use with any suitable surgical instrument including electrosurgical instruments, other ultrasonic surgical instruments, etc.

Ultrasonic surgical instrument 10 generally includes a handle assembly 100 and an elongated assembly 200 extending distally from handle assembly 100. Handle assembly 100 includes a housing 110 defining a body portion 112 configured to support an ultrasonic transducer and generator assembly ("TAG") 300, and a fixed handle portion 114 defining an internal compartment configured to receive a battery (not shown). Handle assembly 100 further includes an activation button 120 operably positioned to electrically couple between TAG 300 and the battery when TAG 300 is mounted on body portion 112 of housing 110 and the battery is engaged within the internal compartment of fixed handle portion 114 of housing 110. A clamp trigger 130 extends from housing 110 of handle assembly 100 adjacent fixed handle portion 114 of housing 110. Clamp trigger 130 extends into body portion 112 of housing 110 and is selectively movable relative to housing 110 to actuate ultrasonic surgical instrument 10.

TAG 300 and the battery are each removable from handle assembly 100 to facilitate disposal of handle assembly 100 after a single use or to enable sterilization of handle assembly 100 for subsequent use. TAG 300 may be configured to withstand sterilization such that TAG 300 may be sterilized for repeated use. The battery, on the other hand, is configured to be aseptically transferred and retained within the internal compartment of fixed handle portion 114 of housing 110 of handle assembly 100 such that the battery may be repeatedly used without requiring sterilization thereof. A locking door 116 provides selective access to the internal compartment of fixed handle portion 114 to enable the insertion and removal of the battery from fixed handle portion 114 of housing 110 and retains the battery within the internal compartment when disposed in the locked condition.

Activation button 120, TAG 300, and the battery are electrically coupled to one another upon engagement of TAG 300 with body portion 112 of housing 110 of handle assembly 100 and engagement of the battery within the internal compartment of fixed handle portion 114 of housing 110. As such, in use, when activation button 120 is activated in an appropriate manner, an underlying two-mode switch assembly (not shown) is activated to supply power from the battery to TAG 300 in either a "LOW" power mode or a "HIGH" power mode, depending upon the manner of activation of activation button 120.

TAG 300 includes a generator and an ultrasonic transducer. The ultrasonic transducer converts a high voltage AC signal received from the generator into mechanical motion that is output to elongated assembly 200, as detailed below. As an alternative to providing TAG 300 and the battery, the transducer of TAG 300 may be disposed on-board handle assembly 100 (integral therewith or removable therefrom) while the generator of TAG 300 is remotely disposed and connected to the transducer via a surgical cable. In such configurations, the battery need not be provided as the generator can be powered by a remote power source, e.g., a wall outlet.

Figure 2:
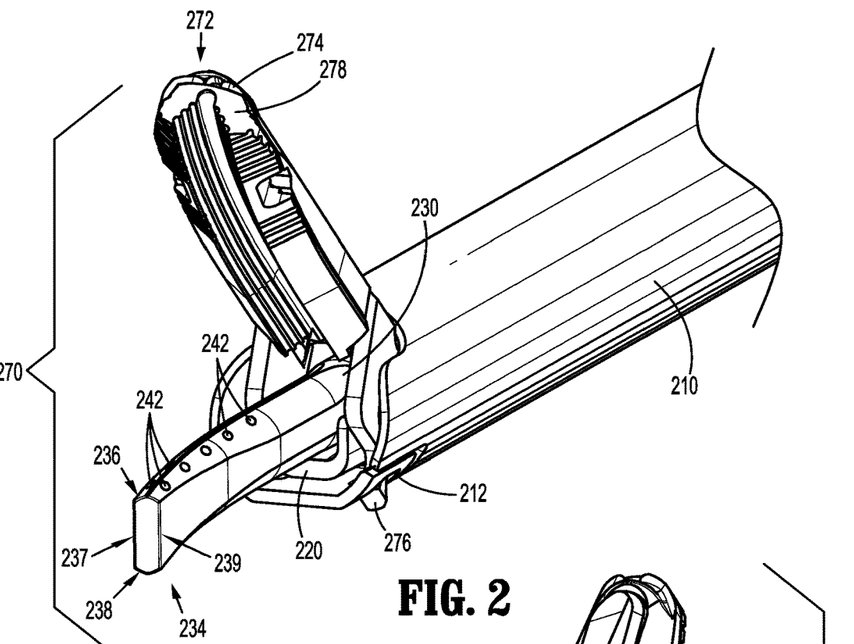
FIG. 2 is an enlarged front, perspective view of the area of detail indicated as "2" in FIG. 1 illustrating an end effector assembly of the ultrasonic surgical instrument.
Figure 3:
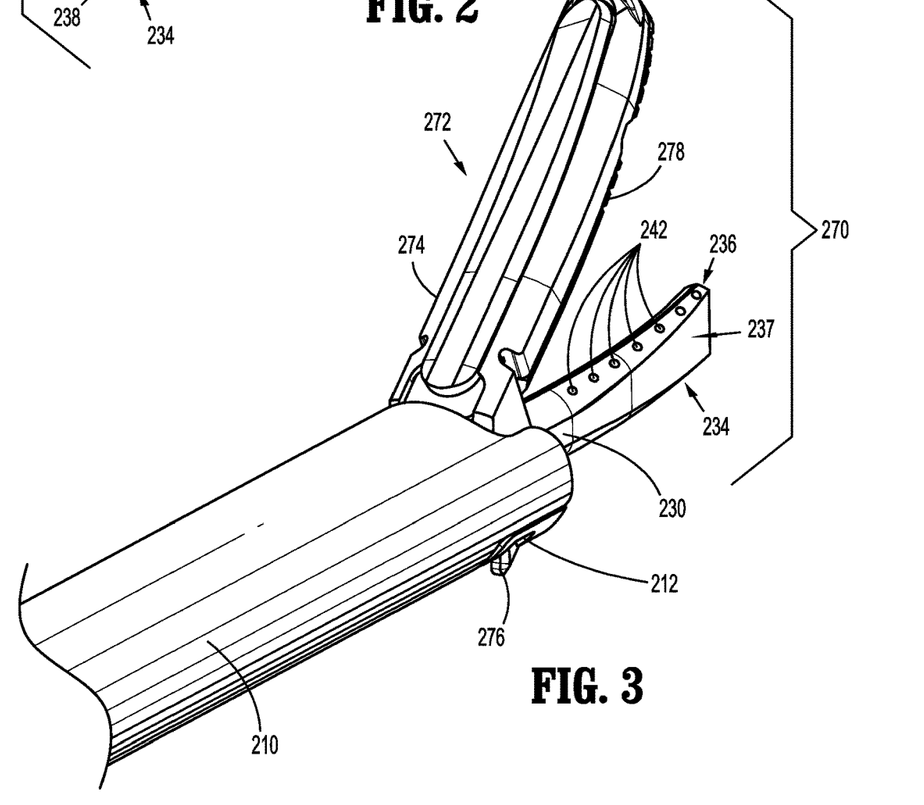
FIG. 3 is an enlarged, rear, perspective view of a distal portion of the ultrasonic surgical instrument of FIG. 1 illustrating the end effector assembly thereof.

With additional reference to FIGS. 2 and 3, elongated assembly 200 includes an outer drive sleeve 210, an inner support sleeve 220 disposed within outer drive sleeve 210 and about which outer drive sleeve 210 is configured to slide, a waveguide 230 extending through inner support sleeve 220, a rotation knob 260 operably coupled about proximal portions of outer and inner sleeves 210, 220, respectively, and an end effector assembly 270 disposed at the distal end of inner support sleeve 220. Elongated assembly 200 is configured such that mechanical motion output from the ultrasonic transducer of TAG 300 is transmitted along waveguide 230 to end effector assembly 270 for treating tissue therewith, such that clamp trigger 130 is selectively actuatable to manipulate end effector assembly 270, and such that rotation knob 260 is selectively rotatable to rotate elongated assembly 200 relative to handle assembly 100. Elongated assembly 200 may be configured as a disposable, single-use component or a reusable component that is sterilizable for subsequent use and may be releasably engagable with handle assembly 100 or integrally affixed thereto.

Outer drive sleeve 210 is operably coupled to clamp trigger 130 within handle assembly 100 at a proximal end portion of outer drive sleeve 210 and is operably coupled with jaw member 272 of end effector assembly 270 at a distal end portion of outer drive sleeve 210, e.g., via receipt of proximal flanges 276 of jaw member 272 within apertures 212 defined within outer drive sleeve 210. Inner support sleeve 220 pivotably supports jaw member 272 at a distal end thereof, e.g., via receipt of pivot bosses (not shown) of proximal flanges 276 of jaw member 272 within corresponding apertures (not shown) defined within inner support sleeve 220. As a result of this configuration, actuation of clamp trigger 130 translates outer drive sleeve 210 about inner support sleeve 220 and urges jaw member 272 to pivot relative to inner support sleeve 220 and blade 234 of waveguide 230 between an open position (FIGS. 2 and 3) and a clamping position for clamping tissue between jaw member 272 and blade 234 of waveguide 230.

Jaw member 272 of end effector 270 includes a more-rigid structural body 274 including proximal flange 276, and a more-compliant jaw liner 278 engaged with more-rigid structural body 274 to oppose blade 234 of waveguide 230 such that, in the clamping position, tissue is clamped between more-compliant jaw liner 278 of jaw member 272 and generally convex top surface 236 of blade 234 of waveguide 230.

Waveguide 230 defines a body (not shown) and a blade 234 extending from the distal end of the body. The body of waveguide 230 is operably coupled to the ultrasonic transducer of TAG 300 within handle assembly 100 and extends distally from handle assembly 100 through inner support sleeve 220. Blade 234 extends from the body of waveguide 230 and distally from inner support sleeve 220 and forms part of end effector 270 in that blade 234 is positioned to oppose jaw member 272 such that pivoting of jaw member 272 from the open position (FIGS. 2 and 3)) to the clamping position enables clamping of tissue between jaw member 272 and blade 234. Blade 234 defines a curved configuration wherein the directions of movement of jaw member 272 between the open and clamping positions are perpendicular to the direction of curvature of blade 234. However, it is also contemplated that blade 234 define a straight configuration or that blade 234 curve towards or away from jaw member 272, that is, where the directions of movement of jaw member 272 between the open and clamping positions are coaxial or parallel to the direction of curvature of blade 234. Multiple curves in one or more planes and/or other suitable configurations of blade 234 are also contemplated.

In embodiments, blade 234 defines a generally convex top surface 236, e.g., the surface that opposes jaw member 272, and a generally convex bottom surface 238 opposite generally convex top surface 236. Generally convex surfaces 236, 238 may each be defined by a pair of surfaces (flat or arcuate surfaces) that converge at an apex, or may be formed by a single arcuate surface defining an apex. Blade 234 further includes side surfaces 237, 239 that are generally smooth and flat except for the curvature of blade 234. Other configurations of blade 234 and the surfaces 236, 237, 238, 239 thereof are also contemplated.

Figures 4A, 4B, 5A:
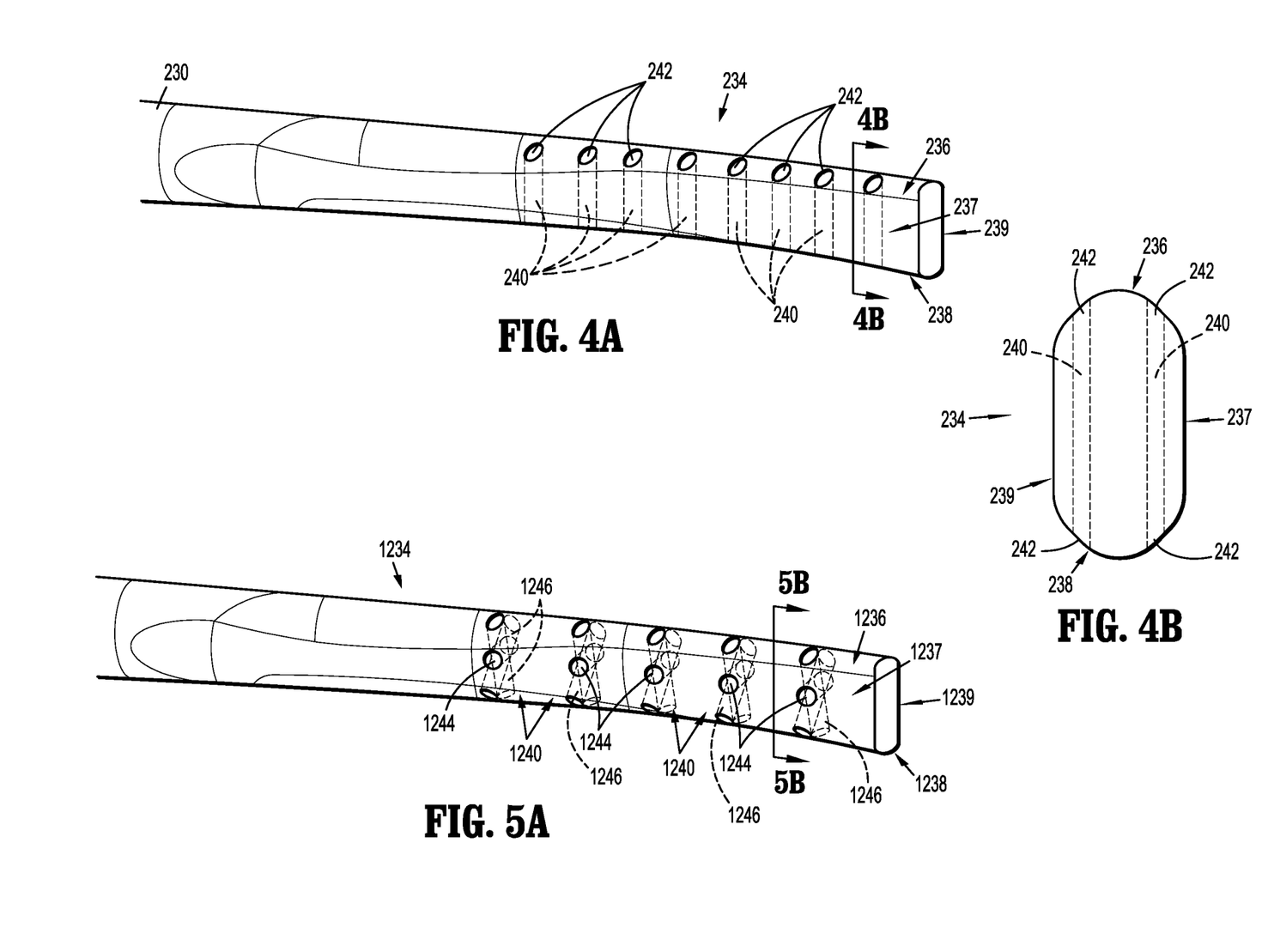
FIG. 4A is a perspective view of a blade of the end effector assembly of the ultrasonic surgical instrument of FIG. 1.
FIG. 4B is a transverse, cross-sectional view taken across section line "4B-4B" of FIG. 4A.
FIG. 5A is a perspective view of another blade configured for use with the ultrasonic surgical instrument of FIG. 1.

Referring also to FIGS. 4A and 4B, blade 234 defines a plurality of lumens 240 extending at least partially therethrough. Any suitable number of lumens 240 may be provided in any suitable pattern (or random distribution) along any portion, portions, or the entirety of blade 234. Lumens 240 may be formed via laser ablation or in any other suitable manner. Each lumen 240 itself or in combination with one or more other lumens 240 communicates with at least two different open ends 242 wherein two of the at least two open ends 242 are defined at different surfaces 236, 237, 238, 239 of blade 234. For example, as illustrated in FIGS. 4A and 4B, each lumen 240 may extend from a first open end 242 at surface 236 to a second open end 242 at surface 238. As another example, lumens 240 may extend from an open end 242 at surface 237 to an open end at surface 239. FIGS. 4A and 4B illustrate two rows of longitudinally-spaced lumens 240 disposed on either side of the apexes of surfaces 236, 238; however, other suitable configurations are also contemplated.

Lumens 240 are configured to draw fluid from one surface 236, 237, 238, 239 of blade 234, through blade 234, to another surface 236, 237, 238, 239 of blade 234 to facilitate cooling blade 234 during use. More specifically, when blade 234 is activated, e.g., ultrasonically vibrated via ultrasonic energy transmitted from TAG 300 (FIG. 1) along waveguide 230 to blade 234, the ultrasonic energy waves propagating through blade 234 and the density changes of the fluid within/across lumens 240 and/or the open ends 242 of lumens 240 serve to urge fluid, e.g., air, vapor, smoke, liquid, other surgical fluids, etc., to flow into open ends 242, through lumens 240, and out other open ends 242. This fluid flow through blade 234 cools blade 234 and is achieved without the need for pumping or other flow systems. Additionally, lumens 240 reduce the mass and increase the surface area of blade 234 as compared to an entirely solid blade and, thus, facilitate radiant cooling of blade 234 after use.

Figure 5B:
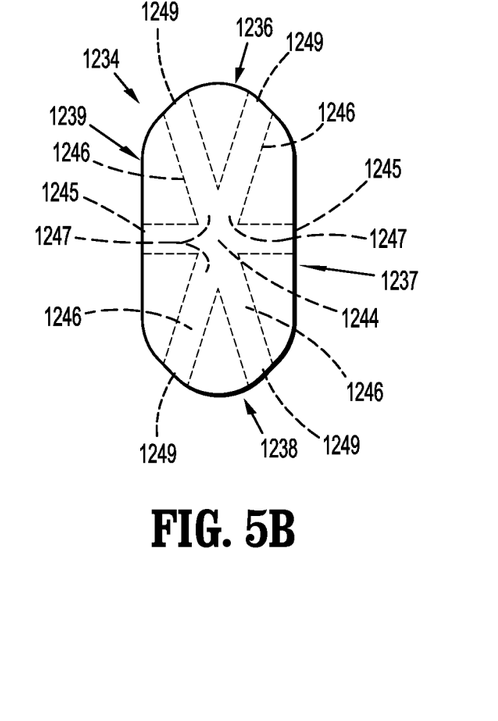
FIG. 5B is a transverse, cross-sectional view taken across section line "5B-5B" of FIG. 5A.

Referring to FIGS. 5A and 5B, another blade 1234 configured for use as the blade of waveguide 230 (FIGS. 2 and 3) or other suitable waveguide is shown including a plurality of lumens 1240 extending at least partially therethrough. The plurality of lumens 1240 of blade 1234, more specifically, include one or more trunk lumens 1244 and one or more branch lumens 1246. Each trunk lumen 1244 may include one or more closed ends terminating within blade 1234 and/or may include one or more open ends 1245 open to one of the surfaces 1236, 1237, 1238, 1239 of blade 1234. Each branch lumen 1246 includes an internal end 1247 disposed in communication with trunk lumen 1244 and an external, open end 1249 open to one of the surfaces 1236, 1237, 1238, 1239 of blade 1234.

When blade 1234 is activated, the ultrasonic energy waves propagating through blade 1234 and the density changes of the fluid within/across lumens 1240 and/or the open ends 1245, 1249 of lumens 1240 serve to urge fluid, e.g., air, vapor, smoke, liquid, other surgical fluids, etc., to flow into open ends 1245, 1249, through lumens 240 (including trunk lumens 1244 and/or one or more branch lumens 1246 communicating with each trunk lumen 1244), and out other open ends 1245, 1249. This fluid flow through blade 1234 cools blade 1234 and is achieved without the need for pumping or other flow systems. Additionally, lumens 1240 reduce the mass and increase the surface area of blade 1234 as compared to an entirely solid blade and, thus, facilitate radiant cooling of blade 1234 after use.

Figure 6:
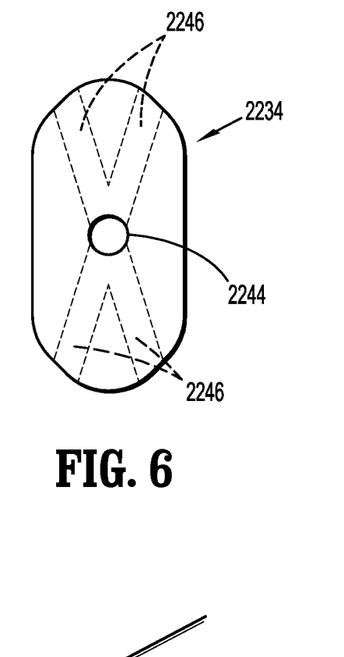
FIG. 6 is a transverse, cross-sectional view of another blade configured for use with the ultrasonic surgical instrument of FIG. 1.

With reference to FIG. 6, another blade 2234 configured for use as the blade of waveguide 230 (FIGS. 2 and 3) or other suitable waveguide is shown including a plurality of lumens 2240 extending at least partially therethrough. Blade 2234 is similar to blade 1234 (FIGS. 5A and 5B) except that, rather than including a plurality of transversely-extending trunk lumens 1244 as in blade 1234 (see FIGS. 5A and 5B), blade 2234 includes one or more longitudinally-extending trunk lumens 2244 having one or more branch lumens 2246 extending therefrom.

Referring generally to FIGS. 1-4B, in use, ultrasonic instrument 10 is advanced into a surgical site and manipulated, e.g., end effector 270 is rotated via rotation of rotation knob 260, such that end effector 270 is positioned with tissue to be treated disposed between jaw member 272 and blade 234 with jaw member 272 disposed in the open position (FIG. 1). Thereafter, clamp trigger 130 is squeezed towards fixed handle portion 114 of housing 110 from an un-actuated position to an actuated position to translate outer drive sleeve 210 about inner support sleeve 220 and relative to end effector 270, thereby pivoting jaw member 272 relative to blade 234 from the open position towards the clamping position to clamp tissue between jaw member 272 and blade 234 and, more specifically, between more-compliant jaw liner 278 of jaw member 272 and generally convex top surface 236 of blade 234.

With tissue clamped between jaw member 272 and blade 234, blade 234 may be activated, e.g., via depression of activation button 120. Upon depression of activation button 120, a DC power signal is supplied from the battery to the generator of TAG 300 which converts the DC power signal into a high voltage AC waveform ultrasonic drive signal that is transmitted to the piezoelectric stack of the ultrasonic transducer of TAG 300. Activation of the piezoelectric stack produces ultrasonic energy that is transmitted along waveguide 230 to blade 234 such that blade 234 is ultrasonically vibrated. The ultrasonic energy provided at blade 234 is used to heat the clamped tissue to treat, e.g., seal and cut, tissue. Blade 234 is also heated when blade 234 is activated. However, lumens 240 facilitate cooling of blade 234 by enabling fluid flow through blade 234 without the need for pumping or other flow systems.

As an alternative or in addition to clamping tissue, top and/or bottom surface 236, 238, respectively, may be positioned in contact with tissue and, with blade 234 activated, moved relative to tissue to dissect tissue.

Figure 7:
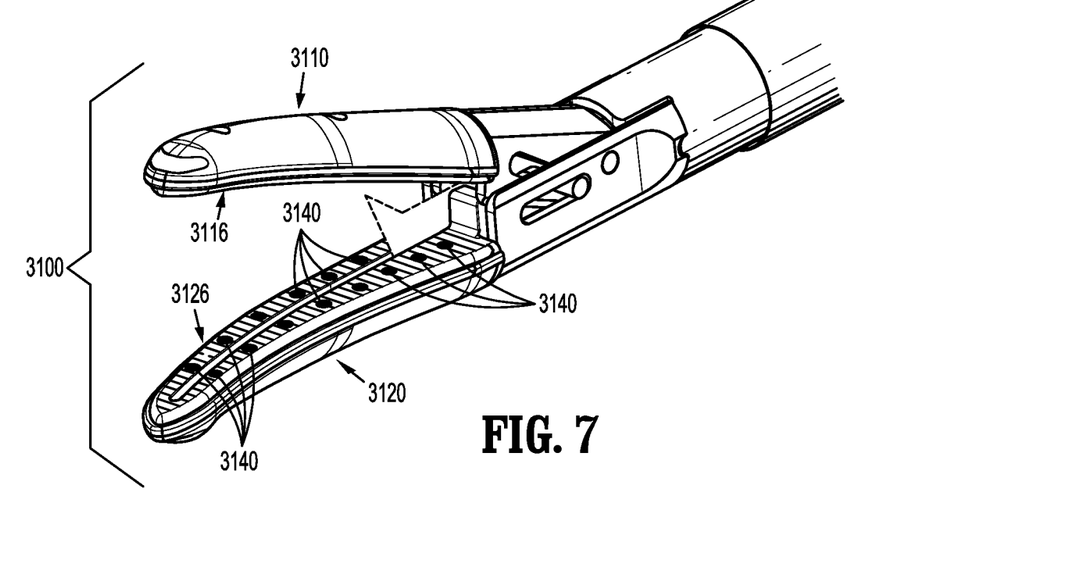
FIG. 7 is a perspective view of a distal end portion of an electrosurgical instrument provided in accordance with the present disclosure, illustrating an end effector assembly thereof.

Turning to FIG. 7, as an alternative to ultrasonic surgical instrument 10 (FIG. 1), as noted above, the aspects and features of the present disclosure may be embodied within other surgical instruments such as an electrosurgical instrument. One example of a suitable electrosurgical instrument includes an end effector assembly 3100 having first and second jaw members 3110, 3120 at least one of which is pivotable relative to the other between an open position and a clamping position for clamping tissue between electrically-conductive bodies 3116, 3126 of the first and second jaw members 3110, 3120, respectively. The electrically-conductive bodies 3116, 3126 are adapted to connect to a source of electrosurgical energy, e.g., an RF generator, to define a bipolar configuration wherein body 3116 is charged to a first electrical potential and body 3126 is charged to a second, different electrical potential such that an electrical potential gradient is created for conducting energy therebetween and through the clamped tissue. Either or both bodies 3116, 3126 may be configured, for example, as plates mounted on jaw members 3110, 3120, respectively, may define solid jaw bodies (that is, the entireties of jaw members 3110, 3120), or may define any other suitable configuration(s). Regardless of the particular configuration, lumens 3140 are defined through either or both bodies 3116, 3126 (according to any of the embodiments detailed above or in any other suitable configuration) to facilitate cooling of bodies 3116, 3126 during use.

From the foregoing and with reference to the various drawings, those skilled in the art will appreciate that certain modifications can be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An ultrasonic surgical instrument, comprising:
   an ultrasonic waveguide defining a blade at a distal end portion thereof, the ultrasonic waveguide configured to transmit ultrasonic energy therealong to the blade, the blade defining a plurality of surfaces including opposing top and bottom surfaces and opposing side surfaces, the top surface defining an apex; and
   at least first and second lumens defined through the blade, the first and second lumens extending, without interruption or intersection by another lumen, through the blade, the first lumen extending from a first open end on the top surface on a first side of the apex to a second open end on the bottom surface to establish a continuous and uninterrupted first flow path through the blade from the first open end to the second open end, the second lumen extending from a third open end on the top surface on a second, opposite side of the apex to a fourth open end on the bottom surface to establish a continuous and uninterrupted second flow path through the blade from the third open end to the fourth open end, the first and second lumens configured to urge fluid through the blade along the respective first and second flow paths between the top and bottom surfaces.

2. The ultrasonic surgical instrument according to claim 1, further comprising:
   a jaw member pivotable relative to the blade between an open position and a clamping position for clamping tissue between the jaw member and the top surface of the blade.

3. The ultrasonic surgical instrument according to claim 2, wherein the jaw member is configured to contact the apex of the top surface.

4. The ultrasonic surgical instrument according to claim 1, further comprising a transducer coupled to the ultrasonic waveguide at a proximal end portion of the ultrasonic waveguide, the transducer configured to produce the ultrasonic energy for transmission along the ultrasonic waveguide to the blade.

5. An ultrasonic surgical instrument, comprising:
an ultrasonic waveguide defining a blade at a distal end portion thereof, the ultrasonic waveguide configured to transmit ultrasonic energy therealong to the blade, the blade extending longitudinally and defining a plurality of surfaces; and
a plurality of spaced-apart lumens defined through the blade, the plurality of spaced-apart lumens spaced longitudinally along the blade such that an entirety of at least one lumen of the plurality of spaced-apart lumens is distally-spaced from an entirety of at least one other lumen of the plurality of spaced-apart lumens, each lumen of the plurality of spaced-apart lumens establishing a flow path through the blade extending from a first open end on one surface of the plurality of surfaces to a second open end on a different surface of the plurality of surfaces, each lumen of the plurality of spaced-apart lumens configured to urge fluid through the blade along the corresponding flow path from the one surface to the different surface, wherein each lumen of the plurality of spaced-apart lumens is fluidly isolated within the blade from each other lumen of the plurality of spaced-apart lumens.

6. The ultrasonic surgical instrument according to claim 5, wherein the one surface is a top surface of the blade and wherein the different surface is a bottom surface of the blade.

7. The ultrasonic surgical instrument according to claim 5, further comprising:
a jaw member pivotable relative to the blade between an open position and a clamping position for clamping tissue between the jaw member and the one surface of the blade.

8. The ultrasonic surgical instrument according to claim 7, wherein the different surface is opposite the one surface.

9. The ultrasonic surgical instrument according to claim 5, further comprising a transducer coupled to the ultrasonic waveguide at a proximal end portion of the ultrasonic waveguide, the transducer configured to produce the ultrasonic energy for transmission along the ultrasonic waveguide to the blade.

10. An ultrasonic surgical instrument, comprising:
an ultrasonic waveguide defining a blade at a distal end portion thereof, the ultrasonic waveguide configured to transmit ultrasonic energy therealong to the blade, the blade extending longitudinally along a longitudinal axis from a proximal end to a distal end and defining a plurality of surfaces;
at least one trunk lumen extending transversely to the longitudinal axis and at least partially through the blade; and
at least one branch lumen extending transversely to the longitudinal axis and at least partially through the blade, wherein the at least one trunk lumen and the at least one branch lumen cooperate to define at least one transverse flow path through the blade extending from a first open end on one surface of the plurality of surfaces to a second open end on a different surface of the plurality of surfaces, the at least one trunk lumen and the at least one branch lumen configured to cooperate to urge fluid transversely with respect to the longitudinal axis and through the blade along the at least one transverse flow path from the one surface to the different surface, wherein the at least one trunk lumen and the at least one branch lumen confine fluid flow within the blade to the at least one transverse flow path and prevent fluid flow through the blade longitudinally along the longitudinal axis distally from the at least one trunk lumen and the at least one branch lumen and proximally from the at least one trunk lumen and the at least one branch lumen.

11. The ultrasonic surgical instrument according to claim 10, further comprising:
a jaw member pivotable relative to the blade between an open position and a clamping position for clamping tissue between the jaw member and the one surface of the blade.

12. The ultrasonic surgical instrument according to claim 11, wherein the different surface is opposite the one surface.

13. The ultrasonic surgical instrument according to claim 10, further comprising a transducer coupled to the ultrasonic waveguide at a proximal end portion of the ultrasonic waveguide, the transducer configured to produce the ultrasonic energy for transmission along the ultrasonic waveguide to the blade.

* * * * *